US005756715A

United States Patent [19]

Monte et al.

[11] Patent Number: 5,756,715
[45] Date of Patent: May 26, 1998

[54] PROCESS FOR MAKING CRYSTALLINE IRON DEXTRAN

[75] Inventors: William T. Monte, Thirdlake; Laurie Scaggs, Lake Villa, both of Ill.

[73] Assignee: Abbott Laboratories, Abbott Park, Ill.

[21] Appl. No.: 747,294

[22] Filed: Nov. 8, 1996

[51] Int. Cl.⁶ .................. C08B 37/02; C07H 1/00
[52] U.S. Cl. .................. 536/113; 536/112; 536/124
[58] Field of Search .................. 536/113, 112, 536/124

[56] References Cited

U.S. PATENT DOCUMENTS

| Re. 24,642 | 4/1959 | London et al. | 536/112 |
|---|---|---|---|
| 2,856,398 | 10/1958 | Novak | 536/113 |
| 2,862,920 | 12/1958 | Berger et al. | 536/113 |
| 2,885,393 | 5/1959 | Herb | 536/113 |
| 3,093,545 | 6/1963 | Westfall et al. | 514/59 |
| 3,574,184 | 4/1971 | Alsop et al. | 536/113 |
| 4,599,405 | 7/1986 | Müller et al. | 536/113 |

FOREIGN PATENT DOCUMENTS 1200902 of 1905 United Kingdom.

*Primary Examiner*—John Kight
*Assistant Examiner*—Everett White
*Attorney, Agent, or Firm*—Michael J. Ward

[57] ABSTRACT

A process for the crystallization of an iron-dextran complex in readily-filterable form comprising adding slowly, with stirring, an acidified aqueous iron-dextran solution to a vessel containing a water miscible organic solvent such as methanol, as well as crystalline iron-dextran complexes so prepared.

26 Claims, No Drawings

PROCESS FOR MAKING CRYSTALLINE IRON DEXTRAN

This application claims the benefit of U.S. application Ser. No. 60/006,518, filed Nov. 9, 1995.

TECHNICAL FIELD

The present invention relates to a process for making iron preparations useful in the treatment of iron deficiencies. More particularly, the invention relates to a process for the preparation of crystalline iron(III)-dextran complex.

BACKGROUND OF THE INVENTION

Iron dextran has been known for about 35 years. It has been utilized primarily as an injectable agent for countering iron deficiencies in animals and human patients, having several advantages over other iron preparations including low toxicity, low incidence of adverse reactions, and satisfactory rate of iron adsorption.

Iron dextran is typically prepared by forming a complex of dextran with iron(III). The dextrans used are generally either (i) partially depolymerized dextrans having a molecular weight in the range of 1,000 to 10,000 or (ii) modified forms of dextran such as hydrogenated dextrans or oxidized dextrans. The iron(III) is prepared by neutralization of an aqueous solution of an iron(III) salt with an alkali. In order to prepare an aqueous iron dextran solution in a form suitable for injection, it is necessary to remove the soluble salts formed in the reaction between the water-soluble ferric salt and the dextran. This can be accomplished by known procedures such as dialysis or reverse osmosis, or by precipitation of the iron dextran complex from the aqueous solution, followed by drying and reconstitution with water.

Isolation of the iron-dextran complex from the aqueous solution by precipitation with a water-miscible solvent is known in the art. U.S. Pat. No. 4,599,405 describes centrifuging and filtering the aqueous iron-dextran solution, followed by precipitation of the complex with ethanol. The complex is then washed with ethanol, separated, and dried to give the iron-dextran complex as a solid which is then reconstituted with water to form an injectable solution.

U.S. Pat. No. 3,093,545 describes isolation of a treacle-like solid iron dextran complex by addition of methanol to the aqueous iron dextran solution, allowing the solid to settle, and decanting the supernatant liquid. The residual solid is then washed with aqueous ethanol, the liquid is decanted, and the process repeated. The residual liquid is removed by vacuum filtration, and the remaining solid complex is dried.

U.S. Pat. No. 3,574,184 describes isolation of a treacle-like solid iron dextran complex by addition of ethanol to the aqueous solution and one or more centrifugation steps.

U.S. Pat. No. 2,885,393 describes a process for making a gelatinous form of an iron dextran complex wherein the complex is purified by precipitation from aqueous solution by addition of isopropanol, followed by decanting the supernatant liquid, redissolving the solid in water, and repeating the process. After further processing, the iron dextran complex is obtained as an aqueous solution.

U.S. Pat. No. Re. 24,642 describes purification of the iron-dextran complex by filtering the aqueous solution, precipitating the complex by mixing with ethanol, filtering the gelatinous solid, and redissolving the complex in water and repeating the precipitation with ethanol. The iron-dextran complex is then dissolved in water to form the injectable solution.

All of the prior art methods for isolating the solid iron-dextran complex require addition of the precipitating solvent to the aqueous iron dextran solution and result in gelatinous or treacle-like solids which are difficult to filter. Alternate methods of solvent removal, such as centrifugation or decantation are therefore required. Substantial further processing of the initial solid is also required to obtain complex of sufficient purity for use as injectable solutions. Consequently, there remains a need for a method of precipitation which produces pure iron dextran complex which can be easily isolated by filtration and dried. The dry powder can then be stored and reconstituted as needed to form the aqueous solution, thereby obviating storage difficulties which result from the prior art methods in which the complex is prepared and/or stored as a 5-to-10% aqueous solution.

SUMMARY OF THE INVENTION

It has now been found that a process in which an iron-dextran complex is added to a solvent, instead of the solvent being added to the iron-dextran complex, unexpectedly results in the formation of an easily-filtered crystalline solid which can be dried to a powder and easily stored for later reconstitution with water. This ease of filtration, and the elimination of the need for reverse osmosis, decanting, or other means of isolation of the solid from the residual aqueous solution, offer a means of considerable cost savings.

Accordingly, in one aspect of the present invention is disclosed a method of making crystalline iron-dextran complex, comprising the steps of:

(a) combining an aqueous solution of dextran in which the dextran has an average molecular of 3,000 to 6,000 with an aqueous solution of an iron(III) salt;

(b) combining the mixture with alkali;

(c) heating and stirring the mixture until the formation of an iron-dextran complex is substantially complete;

(d) acidifying the mixture;

(e) precipitating the iron-dextran complex by adding the mixture to a water miscible solvent; and (f) isolating the crystalline iron-dextran complex.

In another aspect of the present invention is disclosed a process for the crystallization of an iron-dextran complex in readily-filterable form, comprising adding slowly, with stirring, an aqueous iron-dextran solution to a vessel already containing a water miscible organic solvent.

In a further aspect of the present invention are disclosed crystalline iron-dextran complexes prepared by the above processes.

DETAILED DESCRIPTION OF THE INVENTION

Dextran is a polysaccharide polymer of formula $(C_6H_{10}O_5)_n$ composed exclusively of a-D-gluconpyranosyl units linked predominately $\alpha$-1-6 and obtained by the action of bacteria grown on a sucrose substrate by methods well-known in the art. Native dextrans usually have high molecular weight. Lower molecular weight dextrans are prepared by partial depolymerization of the native dextrans by methods known in the art, such as treatment with mineral acid.

A dextran obtained by partial depolymerization of such a native dextran may be further modified, as for example by partial reduction using sodium borohydride or catalytic hydrogenation, or by oxidation. The term "dextran" as used herein is intended to include dextran, reduced dextran, and oxidized dextran. Treatment of unmodified dextran with mild oxidizing agents such as sodium or potassium periodate introduces carboxyl groups on the terminal glucose unit. Optionally, the terminal glucose unit may be oxidized to carboxylic groups using, for example, bromine, sodium hypobromite, sodium bromite, sodium hypochlorite or sodium chlorite. In one embodiment of the invention, dextran is dissolved in water and oxidized by treatment with between about 0.4 and about 0.6 parts per weight (ppw) 5% aqueous sodium hypochlorite, followed by between about 0.10 and about 0.15 ppw of aqueous sodium hydroxide. The oxidation is best carried out at ambient temperature (about 15° to about 35° C.). A representative dextran contemplated for use in the present invention is a partially depolymerized dextran having a molecular weight of between about 1,000 and about 10,000, preferably between about 3,000 and about 6,000.

In accordance with the foregoing, between about 1 and about 10 ppw of such a dextran are dissolved in water (preferred dextrans being unoxidized or oxidized dextrans and oxidized dextrans being most preferred). A particularly preferred embodiment of the process of the present invention utilizes between about 1.0 and about 1.5 ppw of oxidized dextran having a molecular weight of 5,000 to 6,000. The aqueous dextran solution is then added with stirring to an aqueous solution of about 1 ppw of iron(III), where the term "iron(III)" means trivalent hydrous ferric oxide. The iron(III) solution is prepared by neutralizing a ferric salt with alkali. Suitable ferric salts include any water-soluble salts which generate hydrous ferric oxide when treated with alkalis. Representative salts include ferric chloride, ferric nitrate, ferric sulfate, ferric perchlorate, ferric acetate, ferric trichloroacetate, ferric citrate and the like, as well as double salts such as ferric ammonium sulfate or ferric ammonium citrate and the like. Of the above salts, ferric chloride is particularly preferred. Representative alkalis include the hyroxides and carbonates of sodium, lithium and potassium. The ferric salt may be neutralized by treatment with excess alkali, or may be formed in a two step process involving partial neutralization with alkali followed by addition of the dextran solution and additional alkali to achieve complete neutralization and complex formation. The iron(III) solution is preferably prepared by adding between about 0.14 and about 0.24 ppw of aqueous sodium carbonate to an aqueous solution containing about 1 ppw of hydrated ferric chloride.

After combining the aqueous iron(III) and dextran solutions, the mixture is made basic by addition of between about 0.15 and about 0.25 ppw alkali, preferably sodium hydroxide. The mixture is then heated, preferably at between about 80° and about 100° C., and stirred until complex formation is complete. When unoxidized dextran is used, gradual heating may be required to prevent formation of a heterogeneous mixture. The solution may then be acidified using solid, gaseous or liquid acid, preferably aqueous hydrochloric acid, to obtain a pH of between about 4 and about 5. The solution may then be heated, preferably at between about 118° and about 135° C., at a pressure of between about 10 and about 20 psi (68 and 138 KPa). After cooling to ambient temperature, crystalline iron-dextran complex is obtained by adding the reaction solution to a water-miscible organic solvent in a solution-to-solvent ratio of about not less than 1:1 by volume, followed by filtration. Representative solvents include methanol, ethanol, isopropanol, acetone and the like, with methanol being the most preferred solvent and (when methanol is used) the preferred ratio of aqueous iron-dextran solution to solvent being about 1:8. To reduce solvent volume, the aqueous iron-dextran solution may be concentrated prior to addition to the solvent. The initially obtained crystalline iron-dextran may be washed with additional solvent prior to drying and storage.

The process of the present invention will be better understood in connection with the following Examples, which are intended solely as an illustration thereof.

EXAMPLE 1

Preparation of Crystalline Iron-Dextran Complex using Oxidized Dextran

To a solution of molecular weight 5000 Dextran (60.7 g) in water (108 mL) was added bleach (32 mL) and 5% aqueous sodium hydroxide (7.5 mL). The solution was stirred for one hour and then was refrigerated for 17 hours. To a stirred solution of ferric chloride (60 g) in water (300 mL) was added, dropwise over 60 minutes, a solution of sodium carbonate (11.8 g) in water (100 mL), followed by the bleach-dextran solution. To the resulting solution was added a solution of sodium hydroxide (22.6 g) in water (100 mL) over a 60 minute period. The mixture was heated at 90°–100° C. for 90 minutes and then was cooled to ambient temperature and acidified with to pH 4 with HCl to give 907 g of iron-dextran solution. A 447 g aliquot was removed and concentrated to a volume of 160 mL and then was added with stirring to 1038 g of methanol. The resulting crystalline solid was collected by filtration and washed with methanol. The solid was slurried in methanol (173 g), filtered, and dried to afford 15.63 g of iron-dextran powder. The material passed gel permeation chromatographic analysis.

EXAMPLE 2

Preparation of Crystalline Iron-Dextran Complex using Unoxidized Dextran

To a solution in water (70 mL) of ferric chloride (24.0 g) was added a solution of sodium carbonate (4.7 g) in water (40 mL) over an 80-minute period. To the mixture was added a solution of dextran (27.3 g) in water (70 mL), followed by addition, over 40 minutes, of a solution of sodium hydroxide (9.0 g) in water (110 mL). The mixture was then added to methanol (350 mL). The resulting solid was filtered, dissolved in water (150 mL) and heated at 85° C. for 60 minutes. The mixture was cooled and added to methanol (100 mL). The resulting solid was filtered and dried to afford 19.4 g of iron dextran powder. The material passed gel permeation chromatographic analysis.

EXAMPLE 3

Preparation of Crystalline Iron-Dextran Complex with In Situ Oxidation of Dextran To a solution of molecular weight 5000 dextran (27.3 g) in water (70 mL) was added 2.25N aqueous sodium hydroxide (5 mL); the resulting mixture was heated at 75°–80° C. for 30 minutes. The solution was cooled and added to a ferric solution prepared by treating a solution of ferric chloride (24.0 g) in water (70 mL) with 1.1N aqueous sodium carbonate (40 mL). The resulting solution was heated to 80°–90° C., cooled, and added to methanol (100 mL) with stirring. The resulting crystalline solid was filtered and dried to give iron-dextran powder. The material passed gel permeation chromatographic analysis.

EXAMPLE 4

Industrial Preparation of Crystalline Iron-Dextran

To a 30-gallon reactor containing a 25° C. solution under $N_2$ of ferric chloride hexahydrate (5.0 kg) in degassed water (25 kg) was added a solution of sodium carbonate (1.0 kg) in water (8.3 kg). The temperature was maintained at 20°–26° C. while stirring at 30–50 rpm during the addition. In a 50-gallon reactor, dextran (5.2 kg) was dissolved in water (9.1 kg). To the dextran solution was added 5% aqueous sodium hypochlorite (2.9 kg) and after thorough mixing 10% aqueous sodium hydroxide solution (0.7 kg) was added. The solution was stirred until it did not react with KI starch paper. The oxidized dextran solution was then added to the ferric solution over 5 minutes while maintaining the temperature of the ferric solution at 23°–25° C. and stirring at 75–100 rpm. A solution of sodium hydroxide (2.0 kg) in water (8.3 kg) was added over a period of about one hour. The reaction mixture was then stirred for 90 minutes at 21°–26° C. and then was warmed to 85°–100° C. for 90 minutes. The reaction mixture was then cooled to 30°–40° C. and adjusted to pH 4.3–5.0 with HCl.

The reaction mixture was then filtered and the filtrate was heated at 121°–130° C. in a sealed vessel for 80–90 minutes. The solution was concentrated to a volume of about 15 L and cooled to ambient temperature. The iron-dextran solution was then slowly added to 121 kg of methanol over about 60 minutes with vigorous stirring. A precipitate formed instantly. The solid was filtered and rinsed with methanol (120 kg) and then was suspended in 64 kg of methanol. The suspension was stirred for 30 minutes. The solid was filtered and dried in vacuo at 85° C. to give 4.03 kg of iron-dextran powder.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the materials and/or methods of use of the invention, may be made without departing from the spirit and scope thereof.

What is claimed is:

1. A process for the preparation of crystalline iron-dextran complex, comprising the steps of:
   (a) combining an aqueous solution of dextran in which the dextran has an average molecular weight of 1,000 to 10,000 with an aqueous solution of an iron(III) salt;
   (b) combining the mixture with alkali; and
   (c) precipitating the iron-dextran complex by adding the mixture to a water-miscible organic solvent.

2. The process of claim 1 wherein the water-miscible solvent is methanol.

3. The process of claim 1 wherein the dextran is selected from the group consisting of dextran, oxidized dextran, and hydrogenated dextran.

4. The crystalline iron-dextran complex prepared according to the process of claim 3.

5. The process of claim 3 wherein the dextran is oxidized dextran.

6. The crystalline iron-dextran complex prepared according to the process of claim 5.

7. The process of claim 5 wherein the oxidized dextran is prepared by combining sodium hypochlorite and alkali with an aqueous solution of dextran.

8. The crystalline iron-dextran complex prepared according to the process of claim 7.

9. A process for the crystallization of an iron-dextran complex in readily-filterable form, comprising adding slowly, with stirring, an aqueous iron-dextran solution to a vessel containing a water miscible organic solvent.

10. The process of claim 9 wherein the aqueous iron dextran solution is added to the water-miscible organic solvent in a ratio of not less than 1:1 by volume.

11. The process of claim 10 wherein the water-miscible solvent is methanol.

12. The process of claim 11 wherein the aqueous iron dextran solution is added to the methanol in a ratio of about 1:8 by weight.

13. The crystalline iron-dextran complex prepared according to the process of claim 12.

14. A process for the preparation of crystalline iron-dextran complex, comprising the steps of:
   (a) combining an aqueous solution of dextran in which the dextran has an average molecular weight of 3,000 to 6,000 with an aqueous solution of an iron(III) salt;
   (b) combining the mixture with alkali;
   (c) heating and stirring the mixture until the formation of an iron-dextran complex is substantially complete;
   (d) precipitating the iron-dextran complex by adding the mixture to a water-miscible organic solvent; and
   (e) isolating the crystalline iron-dextran complex.

15. The process of claim 14 wherein the water-miscible solvent is methanol.

16. The process of claim 14 wherein the dextran is selected from the group consisting of dextran, oxidized dextran, and hydrogenated dextran.

17. The crystalline iron-dextran complex prepared according to the process of claim 16.

18. The process of claim 16 wherein the dextran is oxidized dextran.

19. The crystalline iron-dextran complex prepared according to the process of claim 18.

20. The process of claim 18 wherein the oxidized dextran is prepared by combining sodium hypochlorite and alkali with an aqueous solution of dextran.

21. The crystalline iron-dextran complex prepared according to the process of claim 20.

22. A process for the crystallization of an iron-dextran complex in readily-filterable form, comprising adding slowly, with stirring, an aqueous iron-dextran solution to a vessel containing a water miscible organic solvent.

23. The process of claim 22 wherein the aqueous iron dextran solution is added to the water-miscible organic solvent in a ratio of not less than 1:1 by volume.

24. The process of claim 23 wherein the water-miscible solvent is methanol.

25. The process of claim 24 wherein the aqueous iron dextran solution is added to the methanol in a ratio of about 1:8 by weight.

26. The crystalline iron-dextran complex prepared according to the process of claim 25.

* * * * *

UNITED STATES PATENT AND TRADEMARK OFFICE
CERTIFICATE OF CORRECTION

PATENT NO. : 5,756,715
DATED : May 26, 1998
INVENTOR(S) : Monte et al.

It is certified that error appears in the above-identified patent and that said Letters Patent is hereby corrected as shown below:

Column 6, line 3, change "A process" to --A process of claim 1--.

Column 6, line 47, change "A process" to--A process of claim 14--.

Signed and Sealed this

Twelfth Day of January, 1999

Attest:

Attesting Officer     *Acting Commissioner of Patents and Trademarks*